(12) United States Patent
Rotondo et al.

(10) Patent No.: US 7,534,038 B2
(45) Date of Patent: May 19, 2009

(54) DENTAL X-RAY APPARATUS AND METHOD OF POSITIONING A PATIENT THEREIN

(75) Inventors: Giuseppe Rotondo, Milan (IT);
Gerardo Rinaldi, Milan (IT); N. Alberto Borghese, Milan (IT); Iuri Frosio, Milan (IT)

(73) Assignee: Gendex Corporation, Washington, DC (US)

( * ) Notice: Subject to any disclaimer, the term of this patent is extended or adjusted under 35 U.S.C. 154(b) by 0 days.

(21) Appl. No.: 11/669,467

(22) Filed: Jan. 31, 2007

(65) Prior Publication Data

US 2007/0183567 A1 Aug. 9, 2007

Related U.S. Application Data

(60) Provisional application No. 60/764,050, filed on Feb. 1, 2006.

(30) Foreign Application Priority Data

Mar. 22, 2006 (EP) .................................. 06005906

(51) Int. Cl.
*A61B 6/08* (2006.01)
(52) U.S. Cl. ........................................ 378/205; 378/38
(58) Field of Classification Search ............. 378/38–40, 378/195–197, 205–206
See application file for complete search history.

(56) References Cited

U.S. PATENT DOCUMENTS

| | | | |
|---|---|---|---|
| 4,831,645 A | 5/1989 | Guenther et al. | |
| 4,985,907 A | 1/1991 | Moteni | |
| 6,088,424 A * | 7/2000 | Postlethwaite et al. | 378/63 |
| 6,493,415 B1 * | 12/2002 | Arai et al. | 378/4 |
| 6,614,875 B2 * | 9/2003 | Suuronen | 378/63 |
| 2001/0036246 A1 * | 11/2001 | Graumann | 378/39 |
| 2004/0190678 A1 | 9/2004 | Rotondo et al. | |
| 2004/0258210 A1 * | 12/2004 | Ritter | 378/198 |
| 2005/0053192 A1 * | 3/2005 | Sukovic et al. | 378/41 |

FOREIGN PATENT DOCUMENTS

| | | |
|---|---|---|
| JP | 2001346796 A1 | 12/2001 |
| JP | 2002034973 A1 | 2/2002 |

* cited by examiner

*Primary Examiner*—Hoon Song
(74) *Attorney, Agent, or Firm*—McNees Wallace & Nurick, LLC (57) ABSTRACT

A dental x-ray apparatus is provided that includes an x-ray system having an x-ray source and x-ray detection means; positioning means for positioning a patient's head in a predefined position with respect to the x-ray system; and at least one video camera for generating video images of the patient's head.

27 Claims, 6 Drawing Sheets

DENTAL X-RAY APPARATUS AND METHOD OF POSITIONING A PATIENT THEREIN

CROSS REFERENCE TO RELATED APPLICATIONS

This application claims the benefit of U.S. Provisional Application No. 60/764,050 filed on Feb. 1, 2006.

BACKGROUND OF THE INVENTION

The present invention relates to a method of positioning a patient in an x-ray apparatus for dental x-ray radiography. The invention further relates to a dental x-ray apparatus for implementing the method.

In dental radiography, a precise position of the patient's head with respect to the radiological apparatus is mandatory to achieve the best focusing and best image quality. The need for controlling the position of a patient has first arisen in the radiotherapy domain. In this field, the X-ray dose can be greatly increased, up to 10 times, if the position of the patient is known with high accuracy. The increased X-ray dosage allows limiting the exposure of healthy tissue to radiation.

Mechanical Systems and Fixed X-Ray Systems

The first system developed for radiotherapy was based on a stereotactic/head frame. This head frame is based on an abstract model to which the actual head and a CAT model are both referred. The head frame allows patient positioning to be achieved with a high accuracy (from 2.5 to 4.5 mm). However, a helmet has to be worn by the patients, which requires a very careful positioning if large positioning errors are to be avoided. This system seems to transfer the problem of the patient's positioning to the positioning of the helmet.

Active Helmets and Movable X-Ray Systems

An alternative solution which is also based on wearing helmets is based on using instrumented helmets (active helmets). These active helmets are very similar to Head Mounted Displays used in Virtual Reality. The active helmets carry magnetic or ultrasound sensors (magnetic sensors are badly distorted by ferromagnetic material, and ultrasound sensors do not appear to be so accurate). However, the use of a helmet or any similar device is not adequate for dental radiography.

2D Radiographic or 2D Video-Imaging and Movable X-Ray Systems

An alternative solution is to use an intelligent video system that surveys the patient and outputs data required for the correction of the location and orientation of the X-ray system. A simple solution is based on computed tomography (CT) data and the patient can be aligned with the machine using 2D radiographies. This approach requires additional 2D radiographies, and does not meet the needs of dental radiography.

Two of the first attempts to use natural video images are described as follows. In the first system, 2D images of the patient face are aligned with 2D reference images (obtained from CT data). Then, an opportune correlation measure is used for aligning the patient's current images with reference ones. In the second system, 2D images of the patient's face are aligned with 2D images of the patient face in a reference condition. The operator then sees on the display the subtraction (difference) images. For this system, reported alignment errors are in the range 1-3 mm. These methods have been recently extended using three video cameras to acquire 2D images.

3D Video Images and Movable X-Ray Systems

More recently, attempts to use 3D digital models of the face, reconstructed in real-time, have been explored. In one system, the 3D reconstruction of the patient's surface in a current position is performed in real-time. This 3D digital model is then aligned with the model of the patient in a reference condition. These systems require that an accurate digital model of the patient be built in real-time. Although automatic 3D scanners have been on the market for few years (e.g., Minolta), their impact on the costs of an x-ray machine is quite high. Moreover, these systems are difficult to operate automatically for several reasons. First, very little information is available for alignment, i.e, the body shape does not have geometrical features (sharp peaks, valleys, etc.), which would allow defining robust error measures, to be used to evaluate alignment. Second, the 3D models are represented as meshes or surfaces. In the first case, the distance between the mesh and the 3D mesh is required, which is an approximate measurement. In the second case, the surface to surface distance has to be determined, which requires a normal to the surface computation that is time consuming.

A simpler way to build a working 3D model, is to resort to passive retro-reflective markers which are positioned onto the patient. The body CT image is acquired with CT and a 3D approximated model of the body segment can be reconstructed and aligned with CAT data. Alternatively, an active pattern (e.g., a grid, a bar code) can be projected over the patient's body. An evolution of these systems, of particular interest in x-ray radiography, is based on substituting the CAT data with laser markers.

Characteristics of Dental X-Ray Systems and Drawbacks Thereof

Up to now, positioning systems for dental panoramic radiographies are based on mechanical systems combined with laser markers. The patient bites a mechanical device that is aligned with the orthopantomographic machine. A set of laser markers are then projected on the head of the patient. The position of the mechanical device (bite block) and of the patient's orientation is manually adjusted by an operator. This operation mode has two main drawbacks. First, the laser markers are projected on the frontal and lateral parts of the face, so the operator has to move around the patient to see if the markers are properly aligned with the patient's head. Second, once this alignment has been achieved and checked, the operator exits from the room where the orthopantomographic apparatus and the patient are located to start the x-ray imaging process. Unfortunately, during this time period before the operator starts the x-ray imaging process, there is a high likelihood that the patient will move out of the proper alignment position for the x-ray imaging process.

Moreover, the possibilities for an operator of the x-ray apparatus to move within the working space of an orthopantomographic system is very restricted, and a good analysis of the patient alignment can be uncomfortable for the operator. Therefore, if the patient is not aligned with the markers, the operator is forced to assume uncomfortable positions in order to help the patient to reach the required position.

Therefore, what is needed is an easy and reliable system and method for positioning and aligning a patient in an x-ray apparatus for dental radiography.

SUMMARY OF THE INVENTION

One embodiment of the present invention is directed to a method of positioning a patient in an x-ray apparatus for dental x-ray radiography. The x-ray apparatus including an x-ray system having an x-ray source and x-ray detection means, a positioning means for positioning the head of a patient in a predefined position with respect to the x-ray system, and at least one video camera for generating images of the head of the patient to be examined. The method including pre-positioning the head of a patient in a patient area of the x-ray apparatus using the positioning means, generating images of the head of the pre-positioned patient from at least one view by the at least one video camera, and aligning the x-ray system and the pre-positioned patient using the images of the head of the patient.

Another embodiment of the invention is directed to a dental x-ray apparatus, including an x-ray system having an x-ray source and x-ray detection means, positioning means for positioning the head of a patient in a predefined position with respect to the x-ray system, and at least one video camera for generating images of the head of the patient to be examined.

In the present invention, one or more video cameras are used for simplifying the alignment of a patient in a dental x-ray apparatus. After pre-positioning the patient in the patient area of the x-ray apparatus using the positioning means, it is no longer necessary that medical personnel moves the patient by hand for achieving correct alignment of the patient with the x-ray system. Whereas in the prior art, alignment has been controlled in real-space, in the present invention alignment is controlled in a data space comprising image data generated by the video camera. Alignment can be remote controlled using the images generated by the at least one video camera and displayed on a display at a control station while moving the x-ray system to align the x-ray system with the patient. The x-ray apparatus of the invention may be adapted, for example, to orthopantomography, scannography, linear tomography, cephalography, and/or dental volume reconstructions.

One advantage of the present invention is that it accelerates the alignment procedure and achieves a higher accuracy of the alignment.

Another advantage of the present invention is that the correct alignment of the patient is monitored during the imaging process and appropriately corrected if necessary.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible, the same reference numbers will be used throughout the drawings to refer to the same or like parts.

DETAILED DESCRIPTION OF THE INVENTION

In one embodiment, the general setup of the x-ray apparatus of the present invention and the kinematic system thereof corresponds to those systems disclosed in U.S. Pat. No. 4,985,907 or U.S. Patent Application Publication No. 2004-0190678 A1 (also published as International Publication No. WO 2004/014232), both of which references are hereby incorporated by reference in their entireties. The x-ray apparatus of the present invention differs from these prior apparatuses in that the present invention includes one or more video cameras that allow an improved and simplified apparatus-patient alignment for radiography, which alignment process may be essentially remote controlled.

The x-ray apparatus of the invention is preferably adapted for the following well-known techniques in dental radiography: orthopantomography, scannography, linear tomography, cephalography, and/or dental volume reconstructions. Preferably, the x-ray apparatus is used with an orthopantomographic, cephalographic or cone beam technique x-ray system.

Figure 1:
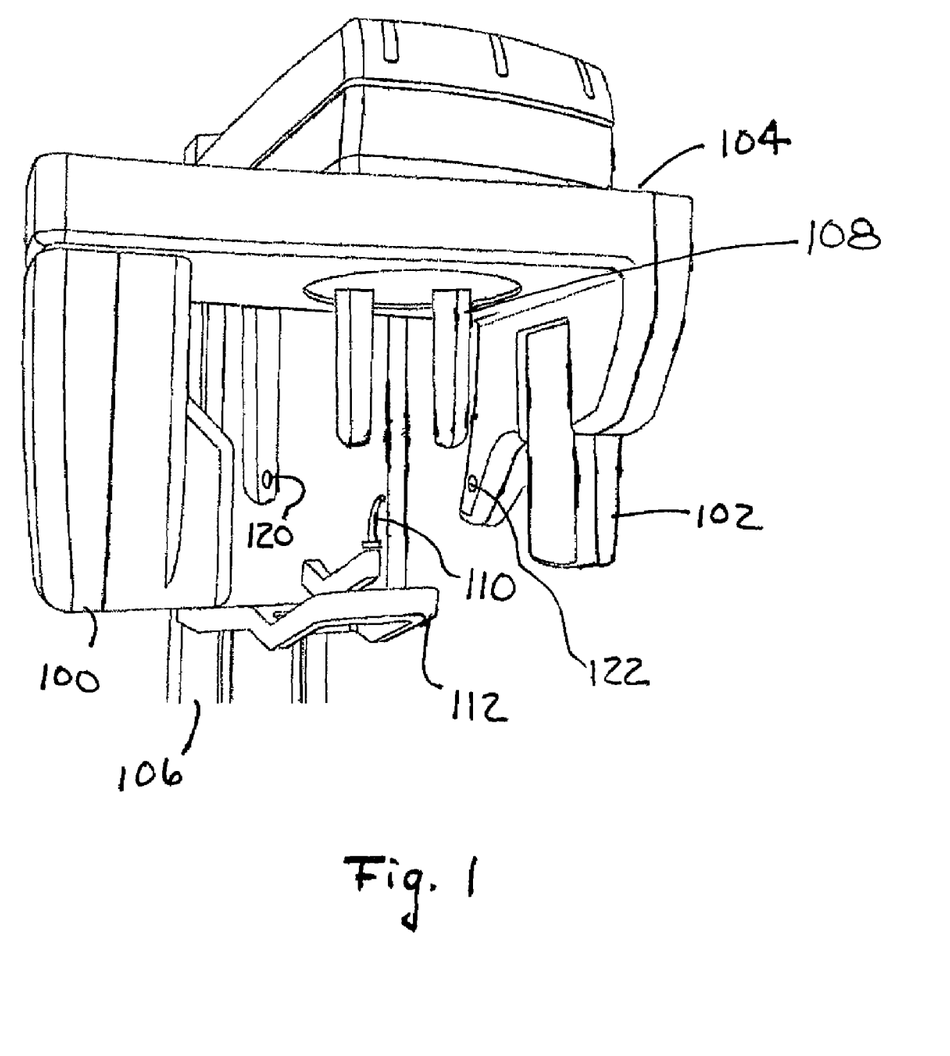
FIG. 1 illustrates an embodiment of a general assembly of an orthopantomographic system.

As shown in FIG. 1, the x-ray system comprises an x-ray source 100 and x-ray detector 102. The x-ray system is movably mounted at opposite ends of a rotating arm (RA) 104 that allows orbital movements of the x-ray system around the head of a patient. The x-ray detector 102 may be a conventional x-ray film cartridge, a digital imager or any other suitable x-ray detection arrangement.

The x-ray apparatus can include several moving mechanisms for the x-ray system. A first moving mechanism is a rotation mechanism to rotate the rotating arm 104 and the x-ray system around a patient's head that has been positioned between the x-ray source 100 and the x-ray detector 102. The rotation mechanism has a rotational axis. A rotation of the x-ray system with respect to a predefined zero-position defines a first rotational position of the x-ray system that may be expressed by an angle or by any other suitable measurement system.

Another moving mechanism is a first translation mechanism to translate the rotational axis of the rotation mechanism in a plane perpendicular to the rotational axis, wherein the translation of the x-ray system within the plane with respect to a predefined zero-position defines a first translational position of the x-ray system, that may be expressed in terms of X-Y coordinates within the plane or by any other suitable measurement system.

Optionally, another moving mechanism is a second translation mechanism to adjust the x-ray system in a vertical direction to the height of a patient. The translation of the x-ray system in the vertical direction with respect to a predefined zero-position defines a second translational position of the x-ray system that may be expressed by its Z-coordinate or by any other suitable measurement system.

Figure 2:
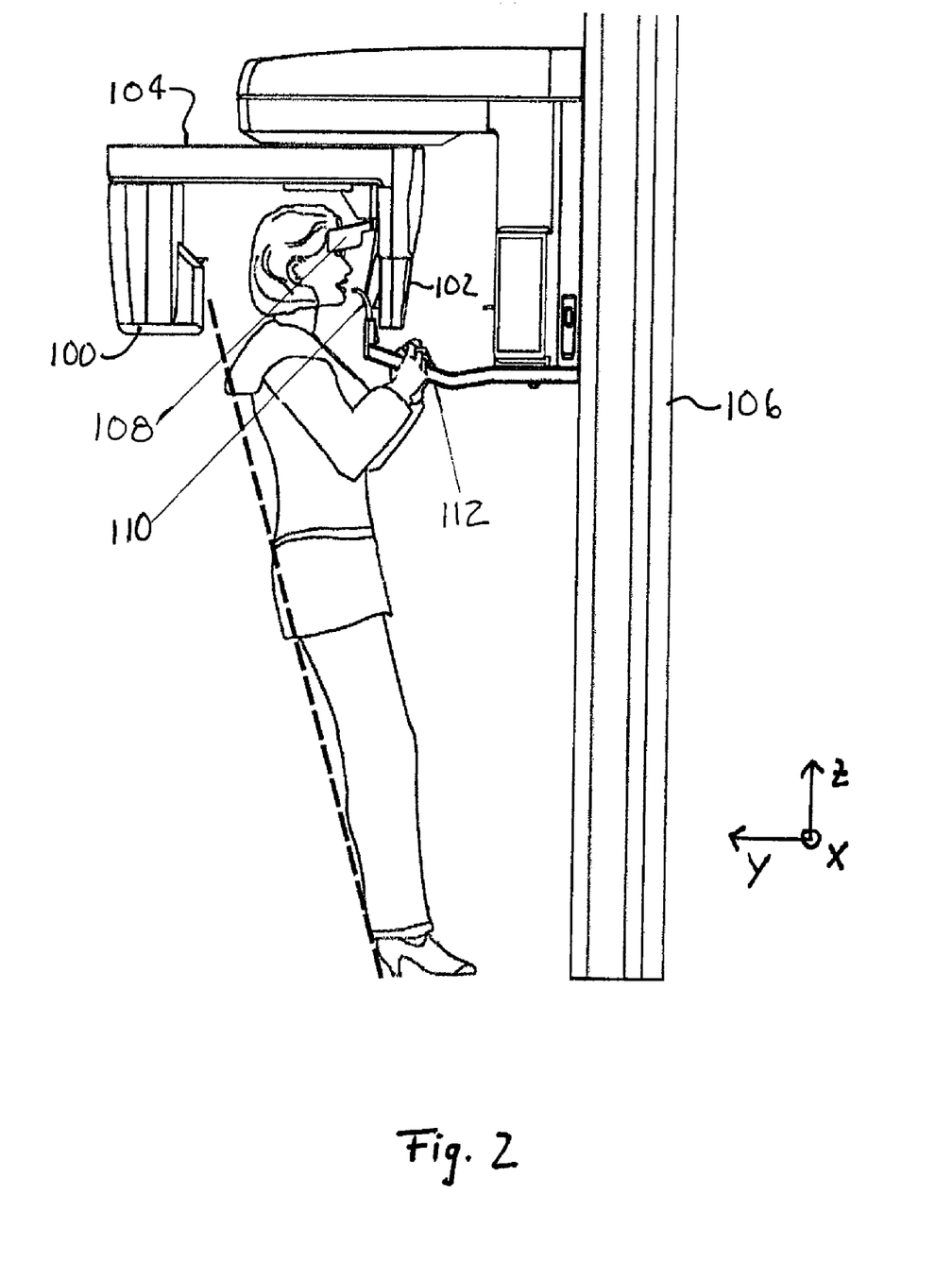
FIG. 2 is a total view on a dental x-ray system with a patient positioned in the patient area.

The coordinate system used for the movement of the x-ray system is similar to the one defined in U.S. Pat. No. 4,985,907, cf. FIG. 2 therein, and US 2004-0190678 (WO 2004/014232), cf. FIG. 2 therein. The coordinate system is an orthogonal coordinate system having a vertical Z axis and, perpendicular thereto, an X-axis and a Y-axis laying in a horizontal plane. One embodiment of the directions of the X and Y-axis is shown in FIG. 2.

In one embodiment, the rotation mechanism, the first translation mechanism and the second translation mechanism may be provided by the kinematic system described in U.S. Pat. No. 4,985,907. In this embodiment, the rotation axis (also referred to herein as the R-axis) of the rotation mechanism is vertical and the plane perpendicular to the rotation axis is horizontal. The first translation mechanism can be used for linear movements of the rotation axis in the X-direction and the Y-direction within the plane (referred to as the X-axis and Y-axis, respectively), whereby curved translational movements within the plane are possible. The second translation mechanism can be used to move the x-ray system in a vertical direction (Z-direction). The second translation mechanism may be provided by a movable column (MC) 106 (see FIG. 1) and serve the purpose of adjusting the x-ray system to the height of the patient and/or for adjusting the alignment of the patient to the Frankfurt plane (see below). The rotation mechanism and the first and second translation mechanisms thus serve the purpose of aligning a patient with the x-ray system and providing the movements of the x-ray system required for radiographic imaging.

In one embodiment, the rotation and translation mechanisms are motor driven (as described in U.S. Pat. No. 4,985, 907), whereby the motor(s) may be controlled by a control system of the x-ray apparatus (see FIG. 6). The rotation and translation mechanisms may have a system for reading and for transmitting any translation and/or rotation movement to the control system, whereby the exact position of the x-ray system with respect to a predefined starting position of the x-ray system is at any time available at the control system.

The x-ray apparatus of the invention preferably has a rotatable arm (RA) 104 carrying the x-ray system. The rotatable arm 104 is used for rotation of the x-ray system around the head of the patient to be examined. FIG. 2 is a view of the kinematic assembly and the rotating arm (RA) 104 carrying the x-ray system. In the background, the movable column (MC) 106 is indicated carrying the kinematic system and the x-ray system. The movable column 106 is movable in vertical (Z) direction for changing the height of the x-ray system.

A positioning arrangement to position the head of the patient can include a headrest 108 that is mechanically connected the movable column MC (FIG. 2) and is independent of the rotatable arm 104. The headrest 108 can include two substantially vertical members for contacting and fixing lateral sides of the head of the patient. In another embodiment, the headrest 108 can have two substantially horizontal members for contacting and fixing lateral sides of the head of the patient. The distance between the members may be changed for fixing and releasing the head of the patient in the headrest 108. The positioning arrangement can also include a bite block 110 the patient bites in with his/her incisors for pre-positioning the patient to the x-ray system. The positioning arrangement can further include a handle 112 to be gripped by the patient. The headrest 108, the bite block 110 and the handle 112 are preferably attached to the kinematic assembly such they can be moved in a vertical direction with the second translation mechanism. The headrest 108, the bite block 110 and the handle 112 are mounted such that they do not move with movements of said first rotation mechanism or said first translation mechanism.

Figure 6:
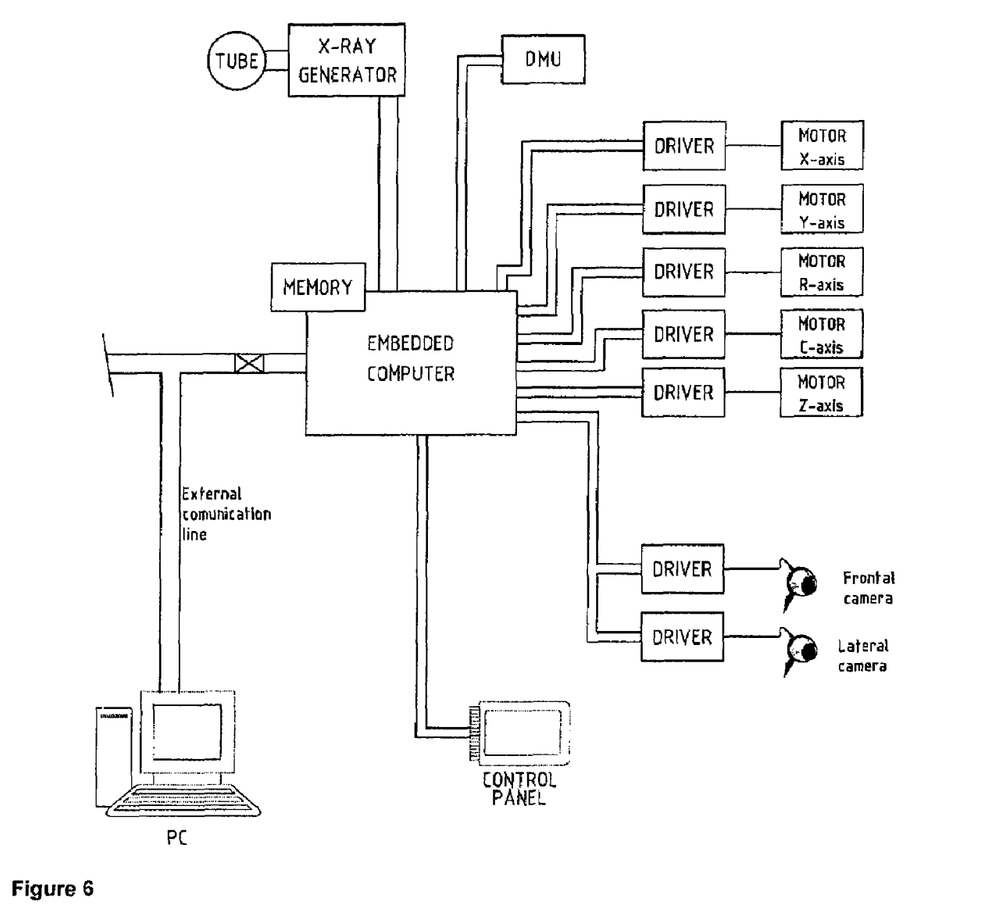
FIG. 6 illustrates one embodiment of a control system for an x-ray apparatus according the invention.

The dental x-ray apparatus of the invention includes a control system depicted schematically in FIG. 6. The embedded computer is generally located close to the mechanical parts of the x-ray apparatus. The control panel includes a display for displaying the image(s) generated by one or more one video cameras, and a control arrangement to permit an operator to control the rotation mechanism, the first and second translation mechanisms, any further movement mechanism (if present), and/or any other function of the x-ray apparatus, e.g., controlling the imaging process. The control panel may be located in a room different or separate from where the x-ray apparatus is located. In one embodiment, the control panel can incorporate the control system and include a computer or microprocessor(s) (also referred to as the "embedded computer") having attached thereto the display for displaying the images generated by the video camera(s). In another embodiment, multiple control arrangements and displays located separate from the control panel can also be used. FIG. 6 depicts schematically a control system similar to that shown in FIG. 3 of US 2004-0190678 (WO 2004/014232). However, the control system of the invention also includes an electrical connection between the at least one video camera and the embedded computer for displaying images generated by the video cameras on the display connected to the embedded computer and for controlling the function of the video camera from the control system. The control system may further include a personal computer (PC) for controlling the x-ray apparatus and for analyzing radiographic images collected by the x-ray system. In addition, as shown in FIG. 6, DMU stands for Digital Module Unit. The DMU preferably includes the x-ray sensor and associated electronics for providing image detection and acquisition.

The embedded computer may be programmed for identification of anatomical reference features of a patient head from the pattern of one or more images of the head of the patient generated by the video camera(s) (see below). From the identified anatomical reference features and the known positions of the video cameras, the position of the identified anatomical reference features may be calculated by the computer in one or more dimensions, such as in the 2-dimensional plane seen by the video camera. In one embodiment, the computer may be programmed for calculating a movement of the x-ray system for aligning the patient and the x-ray system, whereby the movement is calculated from the deviation of the determined position of one or more identified anatomical reference features of the patient and the position of the x-ray system (see further below).

The x-ray apparatus of the invention has at least one system for image acquisition. In a preferred embodiment of the invention, the system for image acquisition is a video camera (for simplicity also referred to as camera). Conventional video cameras, CCD cameras, or CMOS cameras may be used in the present invention. The video camera has an interface for transferring image data, preferably digital image data, to the embedded computer of the control system. The digital image data can be a continuous video feed, a single still image or a periodic providing of still images. The embedded computer can then analyze the image data for the detection of anatomical reference features (see below) or display the images generated by the camera on a display connected to the computer. In one embodiment, the video camera(s) is (are) attached to the rotating arm (RA) 104 such that the cameras move together with the x-ray system. The video cameras may be mounted on the rotating arm 104 using mechanical connectors that allow accurate adjustment of the exact position and viewing direction of the video camera(s). In another embodiment, the video camera(s) is(are) mounted on the apparatus such that they do not move with movements by the rotation mechanism and the first translation mechanism.

The embodiment shown in FIGS. 1 and 2 has two video cameras mounted on the rotating arm 104. Having two video cameras allows viewing the head of a patient from two different directions at the same time. Video camera 1 (one) 120 is mounted on a vertical member attached to the rotating arm (RA) 104. In the orientation of the x-ray system shown in FIG. 1, camera 1 (one) 120 allows the generation of images of the face of a pre-positioned patient. Camera 2 (two) 122 is also attached to the rotating arm 104. In the orientation of the rotating arm 104 shown in FIG. 1, camera 2 (two) 122 allows the generation of images of the right lateral side of the head of a pre-positioned patient. Further, additional video cameras may be installed for simultaneously generating images of the head of a patient from further viewing angles. In one embodiment, since the video cameras are preferably mounted on the rotating arm 104, one video camera may be sufficient for aligning the head of a patient. Images from various viewing angles of the head of a patient may be generated using a single video camera by rotating the rotating arm 104 and thereby bringing the video camera in various positions for viewing the head of a patient. Aligning a patient with the x-ray system is more convenient if the video camera(s) is (are) mounted on the rotating arm 104.

Next, a method of positioning a patient in the x-ray system of the invention and various embodiments thereof will be described. The method of the invention includes pre-positioning the head of a patient in a patient area of the x-ray apparatus using a positioning arrangement, generating images of the head of the pre-positioned patient from at least one view by the at least one video camera, and aligning the x-ray system and the pre-positioned patient using the images of the head of the patient.

Before pre-positioning the patient, the x-ray apparatus may be brought to a starting position, wherein the rotational position of the R-axis and the first translation position are brought to a pre-defined zero-position. In the starting position, the rotational position of the R-axis and the first translation position are pre-optimized for aligning the x-ray system to a standard patient. Pre-positioning also includes adjusting the height of the x-ray system to fit the height of the patient to be examined using the second translation mechanism. The patient then enters the patient area and positions his/her head between the members of the headrest 108. The patient may take the handle 112 of the x-ray apparatus for stabilizing his/her position. Pre-positioning may require that the patient bites, preferably with his/her incisors into a bite block 110 provided at the x-ray apparatus. Since the bite block 110 is provided close to or in the Y-Z plane and oriented such that the patient biting the bite block 110 with his/her incisors is also close to or in the Y-Z plane, the mid-sagittal plane of the patient can be pre-aligned with the Y-Z plane of the x-ray system. The position of the head of the patient may then be fixed by closing the headrest 108.

An operator of the x-ray apparatus may select the type of alignment (e.g., alignment of the mid-sagittal plane to the rotational position of the x-ray system, alignment of the Frankfurt plane to the plane perpendicular to rotation axis R, alignment of canine root position to a first translational position in Y-direction, etc.) to be carried out and select the viewing direction (e.g., frontal, lateral, etc.) by a camera appropriate for the selected type of alignment. For the selected type of alignment, the operator may then generate an image of the patient's head in the selected viewing direction. Preferably, the images generated by the video camera(s) are displayed on a display such as a display of the control panel.

In one embodiment, the alignment step includes identifying at least one anatomical reference feature of the patient's head from one or more images generated by the video camera; comparing the position or orientation of the anatomical reference feature with a translational position of the x-ray system and/or with a rotational position of the x-ray system; and moving the patient and/or the x-ray system for aligning the anatomical reference feature of the patient's head and the x-ray system.

In another embodiment, the aligning step includes displaying the images on a display together with one or more predetermined position marks representing positional information on the x-ray system relative to the video camera. An anatomical reference feature of the patient's head may then be aligned with a rotational or translational position of the x-ray system by moving the patient and/or the x-ray system until the predetermined position marks coincide, on the display, with the anatomical reference feature. Typically, the patient and the x-ray system are aligned in more than one dimension, preferably in two or three dimensions, for achieving a complete alignment required for a selected radiographic technique.

More specifically, an operator of the x-ray apparatus may select the type of alignment to be carried out and select the viewing direction by a camera on the patient accordingly (e.g., frontal, lateral, etc.). For the selected type of alignment, the operator may then display images generated by the video camera on the display. For the selected type of alignment, the control system may also display on the display, position marks representing positional information on the x-ray system relative to the video camera. The position marks displayed relate to the position or orientation of the x-ray system relevant for the selected type of alignment.

The position marks displayed on the display represent, e.g., in the projection of the viewing plane of the camera, a rotational and/or translational position of the x-ray system. The operator of the x-ray apparatus selects the type of position marks to be displayed according to the anatomical reference features to be used for a selected type of alignment (e.g., position marks for the mid-sagittal plane, position marks for the Frankfurt plane, etc.). At a given rotational or translational position of the x-ray system, the position marks indicate on the display, for a predetermined anatomical reference feature of a patient, the position where the predetermined anatomical reference feature should be located in order to be aligned with the x-ray system. Any deviation between the position or orientation of a predetermined anatomical reference feature and the position or orientation of the position marks can then be corrected by moving the x-ray system or the patient. As an example, for aligning the mid-sagittal plane of the patient, the position marks displayed relate to the rotational position of the rotation axis. The position marks indicate an optimum position of a patient relative to the x-ray system in the current position of the x-ray system for the selected type of alignment. Thus, alignment can be achieved by moving the patient such that alignment is achieved in a present rotational and/or translational position of the x-ray system. Alternatively, alignment can be achieved by moving the x-ray system such that alignment is achieved with a present rotational and/or translational position of the patient. In the invention, it is preferred to achieve alignment by moving the x-ray system using the rotation mechanism or the first or second translation mechanism of the x-ray apparatus.

The position marks may be displayed as one or more lines that may be superimposed on the displayed image. The position marks may also be displayed as a grid of parallel lines, or as curved lines. Any deviation between the position marks and the selected anatomical reference features may be discerned on the display by an operator and be used for correcting the position of the x-ray system by actuating the appropriate motor of the appropriate rotation and/or translation mechanism until the position marks coincide, on the display, with the anatomical reference feature.

The accurate identification of an anatomical reference feature on the display may be supported by patches, such as pieces of tape, previously attached at selected positions at the head of the patient, whereby the patches are easily recognizable if the head of the patient is viewed on the display. In this embodiment, the patches may have the function of anatomical reference features. Further or alternatively, alignment may be supported by light signals (such as laser markers) projected on the head of the patient (e.g., on the frontal and/or lateral parts of the face) in a conventional way. The laser(s) may be mounted on the rotating arm 104, whereby the position of the rotating arm 104 required for alignment may be discerned by finding the light signals at the correct positions on the head of the patient. The light signals may be visible on the image displayed on the display. The light signals may support identification of a deviation between the position and/or orientation of the patient in the chosen projection and the target position can be recognized by the operator from the display.

The x-ray system and the patient may then be aligned by adjusting the position of the patient or by adjusting the position of the x-ray system having mounted thereon the video camera. In the first case, the patient is moved such that the relevant anatomical reference features of the patient move, on the display, towards the displayed position marks displayed on the display. In the present invention, it is preferred to perform alignment by moving the x-ray system, since this may be achieved by remote control from the control panel without having to move the patient. In this embodiment, the x-ray system is moved, whereby the position marks displayed on the display move accordingly to the relevant anatomical reference features of the patent's head displayed on the display. In any event, the x-ray system and the head of the patient are aligned until the image of the patient displayed on the display coincides, within predetermined limits of accuracy, with the position marks.

Any aligning of the patient with a target position requires recognizing a deviation of the position or orientation of the patient from the position or orientation of the x-ray system. There are various possibilities for recognizing such a deviation. As noted above, the operator of the x-ray apparatus may recognize such a deviation by comparing on the display the position of the patient, notably predetermined anatomical reference features of the patient, with position marks displayed on the display. For a selected type of alignment, selected anatomical reference features at the patient's head are typically used for describing the position and orientation of the patient's head. As an example, for aligning the Frankfurt plane, the base of the orbita and the acoustic meatus are suitable anatomical reference features. For aligning the mid-sagittal plane, the midpoint between the eyes is a useful anatomical reference feature. For aligning the canine root plane, the canines are the preferred anatomical reference features.

Anatomical reference features may be identified in an image generated from an appropriate viewing angle by a video camera, electronically from the pattern contained in the image. Preferably, anatomical reference features are identified by an operator of the x-ray apparatus from an image of the patient's head displayed on a display.

The movement of the x-ray system required for aligning the patient and the x-ray system may then be determined by an operator by controlling the movement of the x-ray system, via the control system and specifically the control arrangement, using the rotation mechanism and/or the translation mechanisms of the x-ray system. The control system or control arrangement may for example have a joy-stick, whereby the operator may control movement of the x-ray system. While the x-ray system moves, the position marks displayed on the display approach the position of the anatomical reference features of the patient used for the alignment. The operator can move the x-ray system until said position marks displayed on the display coincide with the anatomical reference features of the patient, which may be indicated by the control system by an audible signal.

Alternatively, a movement of the x-ray system required for aligning the patient and the x-ray system may be calculated by a computer from the spatial deviation between the position of the x-ray system and anatomical reference features of the patient input into the computer by an operator by marking, on the display, the anatomical reference feature. This may, for example, be done in that the operator marks on the image displayed on the display, e.g., by a mouse click, a point on the image of the patient, the point defining an anatomical reference feature. If, for example, the mid-sagittal plane of the patient is to be aligned, the operator may click on a point within the mid-sagittal plane of the patient as seen on the display. The computer may then calculate, from the deviation of the position of the point defined by the mouse click and the position marks representing the position of the x-ray system, the movement of the x-ray system required for proper alignment. The operator may then allow the computer to control the calculated movement. In this embodiment, the computer may automatically control the movement required by the x-ray system for achieving the alignment within predetermined error margins. After the computer has completed the automated alignment movement, the operator may manually move the x-ray system to obtain the desired alignment.

In another embodiment, anatomical reference features of the patient are automatically identified by a computer from the pattern of the head of a patient contained in one or more images generated by the video camera. Examples of such anatomical reference features are eyes, the nose, the ears, etc. After having identified one or more suitable anatomical reference features for a predetermined type of alignment, the computer may calculate the spatial position of the identified anatomical reference features and the position of the patient's head. From the location of the identified anatomical reference features as calculated and the position of the x-ray system, the movement of the x-ray system required for alignment can be calculated. The computer may then automatically control the movement required by the x-ray system for achieving the desired alignment within predetermined error margins. The operator of the x-ray apparatus may be informed by an acoustic or visual signal once the movement required for alignment has been completed. The identification of anatomical reference features from the pattern of the head of a patient contained in the images may be supported by patches that are attached at predetermined positions at the head of the patient, whereby the patches are easily recognizable by the computer from the images. The identification of one or more of the patches in the image may allow the computer to identify a predetermined anatomical reference feature that may be used for calculating the required movement for achieving the desired alignment.

The x-ray apparatus of the invention requires calibration. Calibration means defining a selected rotational position of the rotation mechanism as well as selected first and second translation positions of the first and second translation mechanisms as zero-positions, whereby any rotational position (angle of rotation of the R-axis) and translational (in X-, Y- and Z-direction) positions of the x-ray system is known to the computer of the control system. Calibration further requires positioning the camera at a selected position and setting the viewing direction of the camera. Further, the relation between the viewing direction and the rotational and translational position of the x-ray system has to be determined. From the positional information ("positional information" herein refers to information on the rotational position with respect to rotational axis R or on a translational position in X-, Y- or Z-direction of the x-ray system) of the x-ray system and the known position and viewing directions of the video camera, the computer of the control system may calculate the location on the display where the position marks are to be displayed for a selected type of alignment.

One embodiment of an alignment procedure for panoramic dental radiography is described below and includes, in one possible order, alignment of the mid-sagittal plane, the Frankfurt plane and of the canine root position. However, it is also possible to perform these alignment steps in a different order.

Alignment of a pre-positioned patient for orthopantomographic radiography may be performed as follows. First, the mid-sagittal plane may be aligned, beginning with generating an image of the frontal side of a patient's head using the video camera and displaying the generated image on a display together with position marks representing the first rotational position and/or the first translational position of the x-ray system to be aligned with the mid-sagittal plane of the pre-positioned patient; and aligning the first rotational position and/or the first translational position of the x-ray system and the mid-sagittal plane of the pre-positioned patient by moving the x-ray system and/or the patient until the mid-sagittal plane of the patient coincides, on the display, with the position marks.

Another embodiment of aligning the mid-sagittal plane includes generating an image of the frontal side of the head of the patient using the video camera and displaying the generated image on a display together with position marks representing the first rotational position of the x-ray system to be aligned with the mid-sagittal plane of the pre-positioned patient; and aligning the first rotational position of the x-ray system and the mid-sagittal plane of the pre-positioned patient by moving the x-ray system and/or the patient until the mid-sagittal plane of the patient coincides, on the display, with the position marks.

In these embodiments, the x-ray system may be moved by rotating the rotating arm around the rotational axis R, until the mid-sagittal plane of the patient coincides, on the display, with the position marks. The position of the rotation mechanism obtained thereby may be used for determining the movements required for performing the desired orthopantomographic imaging.

Next, the Frankfurt plane may be aligned by generating an image of a lateral side of the patient's head using the video camera and displaying the generated image on a display together with position marks representing the orientation of the plane perpendicular to the rotation axis of the rotation mechanism in the lateral view, whereby the plane is to be aligned parallel to the Frankfurt plane of the patient; aligning the plane parallel to the Frankfurt plane of the patient by moving the x-ray system and/or the patient until the Frankfurt plane of the patient is oriented, on the display, parallel to the position marks.

Figure 4A:
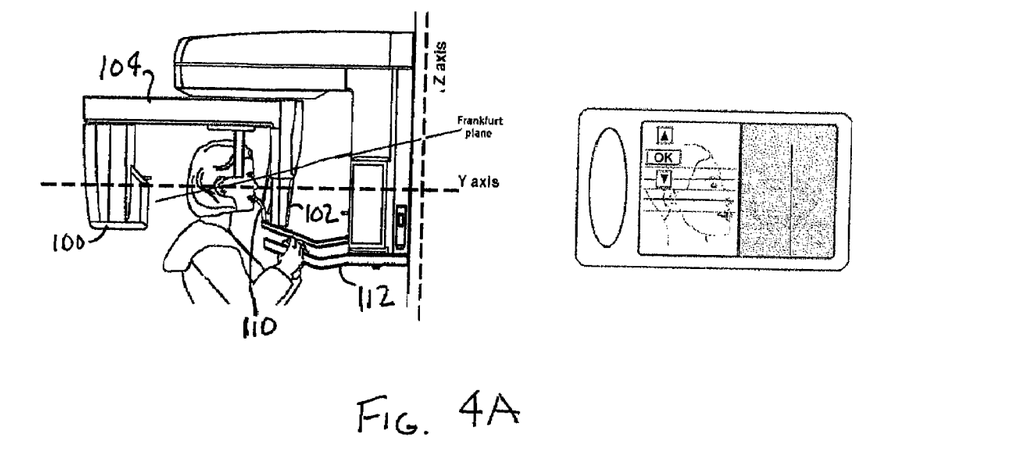
FIGS. 4A and 4B illustrate the alignment of the Frankfurt plane both before alignment (FIG. 4A) and after alignment (FIG. 4B).
Figure 4B:
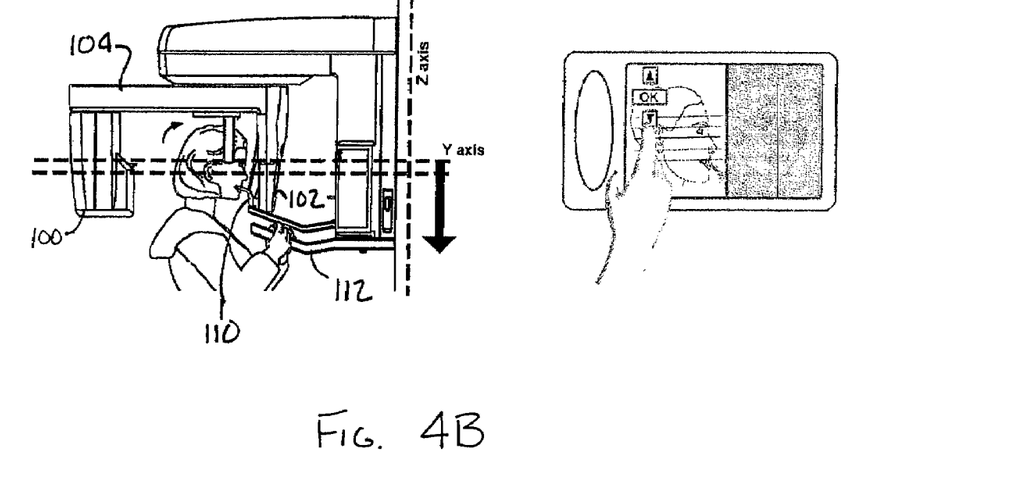

Preferably, the aligning is performed by moving the x-ray system in vertical direction using the second translation mechanism, whereby the patient preferably keeps biting into the bite block, leading to a tilting movement of the patient's head as illustrated in FIG. 4. Preferably, the headrest 108 is released before moving the x-ray system and closed again after having finished alignment. Alignment of the Frankfurt plane ensures that the dental arch is aligned parallel with the X-Y plane.

Next, the canine root plane may be aligned by generating an image of a lateral side of the patient's head using the video camera and displaying the generated image on a display together with position marks for the canine root position, the position marks representing a dimension of the first translational position of the x-ray system to be aligned with the canine root position of the patient; and aligning a dimension of the first translational position of the x-ray system and the canine root position of the patient by moving the x-ray system and/or the patient until the canine root position of the patient coincides, on the display, with the position marks for the canine root position. Preferably, the aligning is performed by moving the x-ray system along the dimension using the first translation mechanism until the canine root position of the patient coincides, on the display, with the position marks. Alignment of the canine root plane corrects for the inclination of the canine roots and ensures that the obtained radiograph displays the canine roots sharply.

In the following, alignment of a patient in the x-ray apparatus of the invention will be described with reference to FIGS. 3A, 3B, 4A, 4B, 5A and 5B for orthopantomographic radiography. The alignment method includes the steps of aligning the midsagittal plane, the Frankfurt plane, and the canine root plane.

Figure 3A:
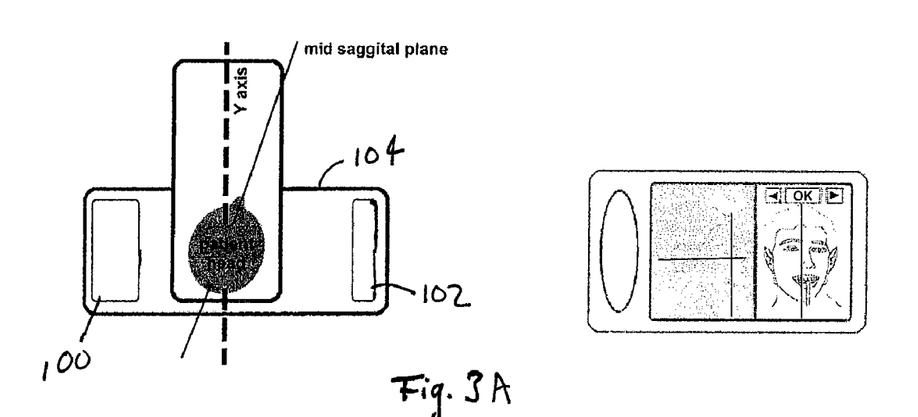
FIGS. 3A and 3B illustrate the alignment of the mid-sagittal plane both before alignment (FIG. 3A) and after alignment (FIG. 3B).
Figure 3B:
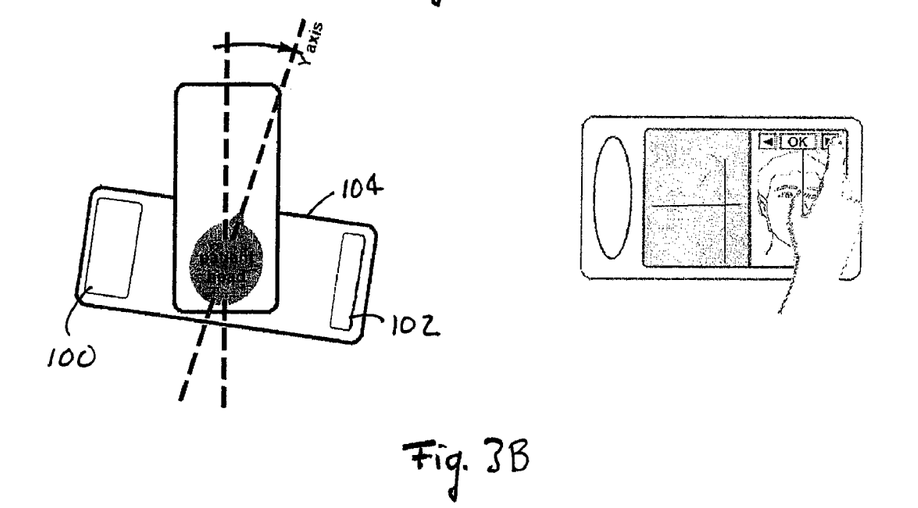

FIGS. 3A and 3B depict the alignment of the mid-sagittal plane. The view on the left-hand side of FIGS. 3A and 3B is along a vertical direction onto the head of the patient showing the positions of the patient's head and the rotating arm 104. The rotating arm 104 is carrying an x-ray source 100 and an x-ray detector 102. On the right-hand side of FIGS. 3A and 3B, a display is shown displaying a frontal view and a lateral view of the head of patient from two video cameras that are not shown. As shown in FIGS. 3A and 3B, the left-hand side of the display showing the lateral view of the patient is grey, indicating that this side of the display is currently inactive. The right-hand side of the display showing the frontal view on the face of the patient is required for the alignment of the mid-sagittal plane and is therefore active. The image of the frontal view of the patient contains a vertical line indicating the position marks of the mid-sagittal plane of the patient. A deviation between the position marks and the mid-sagittal plane of the patient is recognizable on the display. In the embodiment shown, the x-ray system is aligned with the patient in that the x-ray system is moved while the patient is not moved. FIG. 3B shows alignment of the mid-sagittal plane of the patient with the position marks by operator-controlled rotation of the rotating arm (RA) 104 around a vertical rotation axis that coincides with the Z-direction of the system of coordinates. Rotation of the x-ray system with the rotating arm 104 moves the vertical line indicating the position marks to the mid-sagittal plane of the patient. The operator activates the control arrangement, which in this embodiment is a button(s) on the display that acts as a touch screen. The operator stops activating the button(s) when the mid-sagittal plane of the patient coincides with the position marks indicated by the vertical line on the display. This embodiment allows alignment of the mid-sagittal plane without having to move the patient.

FIGS. 4A and 4B show a view from a lateral side on the patient's head (left-hand side) and illustrate alignment of the Frankfurt plane. A patient has been prepositioned and her mid-sagittal plane has been aligned, e.g., as described with reference to FIGS. 3A and 3B above. As indicated by dashed lines, the Y-axis is horizontally oriented and the Z-axis is vertically oriented. Also indicated is the headrest HR 108, a bite block 110 the patient bites into, and a handle 112 that is used by the patient for stabilizing her position. On the right-hand sides of FIGS. 4A and 4B, the display is shown wherein the half of the display showing the lateral view of the patient his active, while the frontal view is inactive. The Frankfurt plane of the patient is the plane that passes, in the lateral view of the patient's head, through the base of the orbita and the acoustic meatus. The Frankfurt plane of the patient has to be aligned such that it is parallel to the X-Y plane of the dental apparatus. Since the X-Y plane is horizontal in this case, the Frankfurt plane of the patient has to be aligned such that it is horizontal. As can be seen on the left-hand side of FIG. 4A, the horizontal dashed line passes close to the acoustic meatus but not through the base of the orbita. The display on the right-hand side of FIG. 4A shows horizontal position marks for the Frankfurt plane in the form of a number of parallel lines. These position marks are not parallel to the Frankfurt plane of the patient.

FIG. 4B shows alignment of the Frankfurt plane by an operator-controlled vertical movement of the x-ray system downwards using the movable column (MC) 106 as the second translation mechanism of the invention. The operator should release the headrest 108 for allowing a movement of the patient's head. The operator activates the control arrangement, i.e., a button(s) on the display that acts as a touch screen. This movement also moves the bite block downwards, whereby the head to the patient is tilted as indicated by the curved arrow near the head of the patient on the left hand side of FIG. 4B. The operator stops activating the button(s) when the Frankfurt plane of the patient is horizontal. After having achieved the desired alignment, the headrest 108 should be closed for fixing the position of the patient's head.

Figure 5A:
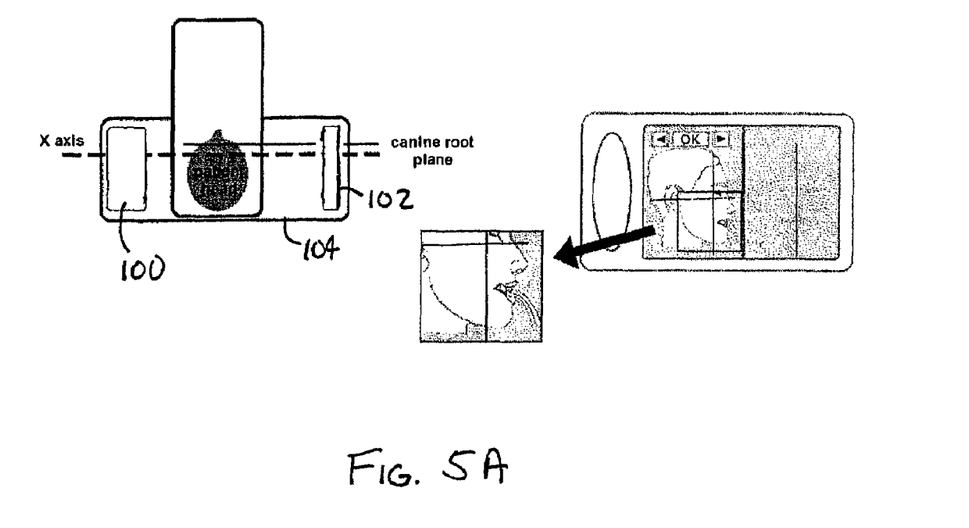
FIGS. 5A and 5B illustrate the alignment of the canine root plane both before alignment (FIG. 5A) and after alignment (FIG. 5B).
Figure 5B:
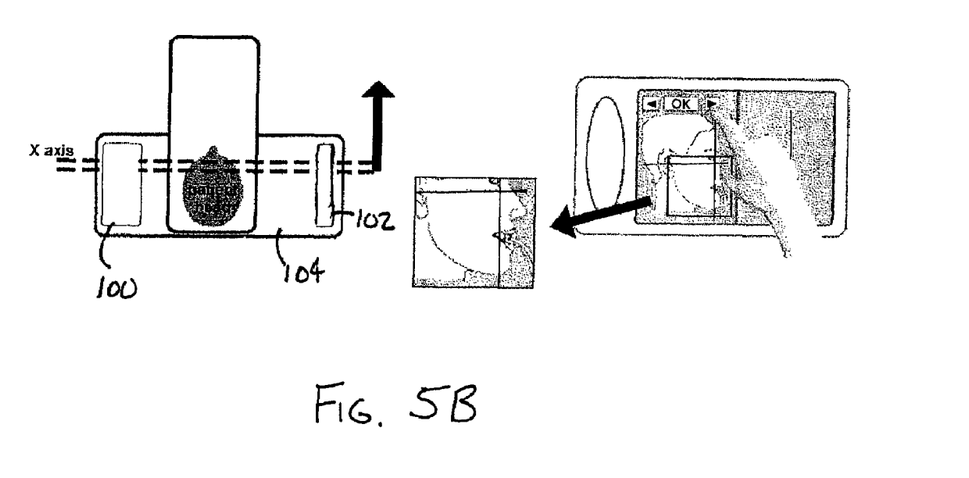

FIGS. 5A and 5B illustrate alignment of the canine root plane. The left-hand side of FIGS. 5A and 5B shows the view along the Z-axis from the top onto the patient. The rotating arm 104 is oriented along the X-axis. The canine root plane is an X-Z plane that passes through the canine roots. On the right-hand side of FIGS. 5A and 5B, the part of the display showing the lateral view or the head of the patient is the active view. In addition, the part of the lateral view showing the area of the mouth may be enlarged by zooming in. The vertical line (position mark) shown on the display should be aligned such that it passes through the canine root. FIG. 5B shows alignment of the canine root plane of the patient with the position mark by operator-control movement of the x-ray system along the Y-axis within a horizontal plane. The operator activates the control arrangement, i.e., a button(s) on the display that acts as a touch screen. The operator stops activating the button(s) when the canine root plane of the patient coincides with the position mark indicated by the vertical line on the display.

In another embodiment of the present invention, the display on the control panel can include more than one active view, thereby permitting an operator to execute more than one alignment operation substantially simultaneously. For example, an operator can align the mid-sagittal plane and the Frankfurt plane at the same time by using both an active front view and an active lateral view provided by the video cameras. Furthermore, the substantially simultaneous alignment of both the mid-sagittal plane and the Frankfurt plane can be completed because the rotational mechanism and the first and second translational mechanisms are each independently controlled.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method of positioning a patient in an x-ray apparatus for dental scanning procedures, the method comprising the steps of:
   providing an x-ray system comprising an x-ray source and x-ray detector, a positioning arrangement to position a patient's head in a predefined position with respect to the x-ray system, and at least one video camera to generate video images of the patient's head;
   pre-positioning the patient's head in a patient area of the x-ray apparatus using the positioning arrangement;
   generating at least one image of the head of the pre-positioned patient from at least one view by the at least one video camera;
   comparing the at least one generated image of the patient's head and a position of the x-ray system; and
   aligning the x-ray system and the pre-positioned patient using the at least one image generated of the patient's head and the position of the x-ray system.

2. The method according to claim 1, wherein the x-ray apparatus comprises:
   a rotation mechanism defining a rotational axis, the rotation mechanism being configured to rotate the x-ray system around the patient's head, the patient's head being positioned between the x-ray source and the x-ray detector, wherein a rotation of the x-ray system with respect to a predefined zero-position defines a first rotational position of the x-ray system;
   a first translation mechanism to translate the rotational axis in a plane perpendicular to the rotational axis, wherein a translation of the x-ray system within the plane with respect to a predefined zero-position defines a first translational position of the x-ray system; and
   a second translation mechanism to vertically adjust the x-ray system to the height of a patient.

3. The method according to claim 1, comprising:
   identifying at least one anatomical reference feature of the patient's head from the at least one image generated by the at least one video camera;
   comparing a position or orientation of the at least one anatomical reference feature with at least one of a translational position of the x-ray system or a rotational position of the x-ray system; and
   moving at least one of the patient or the x-ray system to align the at least one anatomical reference feature of the patient's head and the x-ray system in response to the comparison of the position or orientation of the at least one anatomical reference feature with at least one of a translational position of the x-ray system or a rotational position of the x-ray system.

4. The method according to claim 1, further comprising projecting a light signal pattern on the head of the patient to correspond to anatomical reference features, the light signals being visible in the at least one image generated by the at least one video camera.

5. The method according to claim 1, further comprising displaying on a display the at least one image generated by the at least one video camera together with one or more predetermined position marks representing positional information of the x-ray system relative to the at least one video camera.

6. The method according to claim 5, further comprising aligning at least one anatomical reference feature of the patient's head with at least one of a preselected rotational or preselected translational position of the x-ray system by moving at least one of the patient or the x-ray system until the one or more predetermined position marks coincide, on the display, with the at least one anatomical reference feature.

7. The method according to claim 5, wherein the aligning step comprises:
  generating a frontal image of the patient's head using the at least one video camera and displaying the generated frontal image on a display together with one or more predetermined mid-sagittal position marks representing at least one of a first rotational position or a first translational position of the x-ray system to be aligned with a mid-sagittal plane of the pre-positioned patient; and
  aligning the at least one of the first rotational position or the first translational position of the x-ray system and the mid-sagittal plane of the pre-positioned patient by moving at least one of the x-ray system or the patient until the mid-sagittal plane of the patient coincides, on the display, with the one or more predetermined mid-sagittal position marks.

8. The method according to claim 7, wherein the step of aligning the at least one of the first rotational position or the first translational position includes rotating the x-ray system using a rotation mechanism until the mid-sagittal plane of the patient coincides, on the display, with the one or more predetermined mid-sagittal position marks.

9. The method according to claim 5, wherein the aligning step comprises:
  generating a lateral image of the patient's head using the at least one video camera and displaying the generated lateral image on a display together with one or more predetermined Frankfurt position marks representing an orientation of a plane perpendicular to the rotational axis of a rotation mechanism in a lateral view; and
  aligning the plane perpendicular to the rotational axis parallel to the Frankfurt plane of the patient by moving at least one of the x-ray system or the patient until the Frankfurt plane of the patient is oriented, on the display, parallel to the one or more predetermined Frankfurt position marks.

10. The method according to claim 9, wherein the step of aligning the plane perpendicular to the rotational axis includes moving the x-ray system in a vertical direction using a translation mechanism, resulting in a tilting movement of the patient's head.

11. The method according to claim 10, further comprising the steps of releasing a headrest of the positioning arrangement before moving the x-ray system and closing the headrest again after having finished aligning the plane perpendicular to the rotational axis.

12. The method according to claim 5, wherein the aligning step comprises:
  generating a lateral image of the patient's head using the at least one video camera and displaying the generated lateral image on a display together with one or more predetermined canine position marks for the canine root position, the one or more predetermined canine position marks representing a dimension of the first translational position of the x-ray system to be aligned with a canine root position of the patient;
  aligning a dimension of the first translational position of the x-ray system and the canine root position of the patient by moving at least one of the x-ray system or the patient until the canine root position of the patient coincides, on the display, with the one or more predetermined canine position marks for the canine root position.

13. The method according to claim 12, wherein the step of aligning a dimension of the first translational position of the x-ray system includes moving the x-ray system using a translation mechanism until the canine root position of the patient coincides, on the display, with the one or more predetermined canine position marks.

14. The method according to claim 3, wherein the step of identifying at least one anatomical reference feature of the patient's head from the at least one image generated by the at least one video camera comprises at least one of:
  identifying at least one anatomical reference feature of the patient's head with a computer from a pattern included in the at least one image generated by the at least one video camera and determining spatial positions of the identified at least one anatomical reference feature by the computer; or
  identifying at least one anatomical reference feature of the patient's head with a computer from patches attached at selected positions to the patient's head, the patches being recognizable by the computer in the at least one image.

15. The method according to claim 14, further comprising calculating a movement of the x-ray system required for aligning the patient and the x-ray system from the spatial position of the identified at least one anatomical reference feature and the position of the x-ray system.

16. The method according to claim 3, wherein the step of identifying at least one anatomical reference feature of the patient's head from the at least one image generated by the at least one video camera comprises at least one of:
  identifying at least one anatomical reference feature of the patient's head visually by an operator from an anatomy of the patient's head shown in the at least one image displayed on the display; or
  identifying at least one anatomical reference feature of the patient's head visually by an operator from patches attached at selected positions to the patient's head in the at least one image displayed on the display.

17. The method according to claim 3, wherein the step of moving at least one of the patient or the x-ray system to align the anatomical reference feature of the patient's head and the x-ray system comprises at least one of:
  moving the x-ray system interactively under operator control until a desired coincidence of a selected anatomical reference feature and a position mark representing positional information of the x-ray system is achieved on the display; or
  moving the x-ray system with a computer in response to a calculated movement, the calculated movement being determined based on a calculation by a computer from a difference between the position of the x-ray system and the location of an anatomical reference feature input into the computer by an operator by marking, on the display, the anatomical reference feature.

18. The method according to claim 3, further comprising indicating achievement of alignment of the x-ray system and the pre-positioned patient within predefined error margins to an operator by a visual or audible signal.

19. A dental x-ray apparatus, comprising:
  an x-ray system comprising an x-ray source and an x-ray detector;
  a positioning arrangement to position a patient's head in a predefined position with respect to the x-ray system;
  at least one video camera to generate video images of the patient's head; and
  wherein the generated video images of the patient's head are used to adjust the position of the x-ray system to align the patient's head and the x-ray system for a scanning procedure by comparing the generated video images of the patient's head and the position of the x-ray system.

20. The dental x-ray apparatus according to claim 19, comprising:
 a rotation mechanism defining a rotational axis, the rotation mechanism being configured to rotate the x-ray system around the patient's head, the patient's head positioned between the x-ray source and the x-ray detector;
 a first translation mechanism to translate the rotational axis in a plane perpendicular to the rotational axis; and
 a second translation mechanism to vertically adjust the x-ray system to the height of a patient.

21. The dental x-ray apparatus according to claim 20, wherein the at least one video camera is mounted on the x-ray system and is rotatable by the rotation mechanism.

22. The x-ray apparatus according to claim 20, comprising a control panel with a display to display the generated video images by the at least one video camera, the control panel being configured to permit an operator to control the rotation mechanism and the first and second translation mechanisms.

23. The x-ray apparatus according to claim 19, wherein the x-ray apparatus is adapted for at least one of orthopantomography, scannography, linear tomography, cephalography, dental volume reconstructions using cone beam technique.

24. The x-ray apparatus according to claim 19, comprising control means for controlling movement of the x-ray system.

25. The x-ray apparatus according to claim 19, wherein the at least one video camera comprises two video cameras, the two video cameras being configured and disposed to permit an operator to view the patient's head from two different directions at one time.

26. The x-ray apparatus according to claim 19, comprising a computer programmed to identify anatomical reference features of the patient's head from the generated video images of the at least one video camera.

27. The x-ray apparatus according to claim 26, wherein the computer is programmed to calculate a movement of the x-ray system to align the patient and the x-ray system, the movement of the x-ray system is determined from the deviation of a determined position or orientation of an anatomical reference feature and a position or orientation of the x-ray system.

* * * * *